United States Patent
Vaillancourt

(10) Patent No.: US 6,811,545 B2
(45) Date of Patent: Nov. 2, 2004

(54) SAFETY NEEDLE

(76) Inventor: Vincent L. Vaillancourt, 14 Bunyan Dr., Livingston, NJ (US) 07039

(*) Notice: Subject to any disclaimer, the term of this patent is extended or adjusted under 35 U.S.C. 154(b) by 0 days.

(21) Appl. No.: 10/059,710

(22) Filed: Jan. 29, 2002

(65) Prior Publication Data

US 2003/0120222 A1 Jun. 26, 2003

Related U.S. Application Data

(60) Provisional application No. 60/265,400, filed on Jan. 31, 2001.

(51) Int. Cl.[7] .......................... A61M 5/178; A61M 5/00
(52) U.S. Cl. .................. 604/158; 604/263; 604/171
(58) Field of Search ............................ 604/110, 158, 604/171, 198, 263, 264, 272, 274, 167.01–167.04, 170.01–170.03, 164.01, 164.06, 164.07, 164.12; 600/585; 606/167, 182, 185

(56) References Cited

U.S. PATENT DOCUMENTS

| | | | | |
|---|---|---|---|---|
| 3,792,703 A | * | 2/1974 | Moorehead | 604/158 |
| 4,700,694 A | * | 10/1987 | Shishido | 600/104 |
| 5,586,991 A | * | 12/1996 | Yoon | 606/185 |
| 5,685,852 A | * | 11/1997 | Turkel et al. | 604/159 |
| 5,713,368 A | * | 2/1998 | Leigh | 606/185 |
| 6,398,743 B1 | * | 6/2002 | Halseth et al. | 604/164.12 |

* cited by examiner

Primary Examiner—Brian L. Casler
Assistant Examiner—Matthew F DeSanto
(74) Attorney, Agent, or Firm—Francis C. Hand; Carella, Byrne, Bain, et al

(57) ABSTRACT

The safety needle employs a manually operable actuator that can be depressed into a housing in order to release a spring-biased slider that carries a hollow needle. Upon release, the slider moves into a position to retract the needle over a blunt cannula so that the blunt cannula protects against cutting by the needle. An actuator guard may also be employed to prevent inadvertent actuation of the actuator.

17 Claims, 8 Drawing Sheets

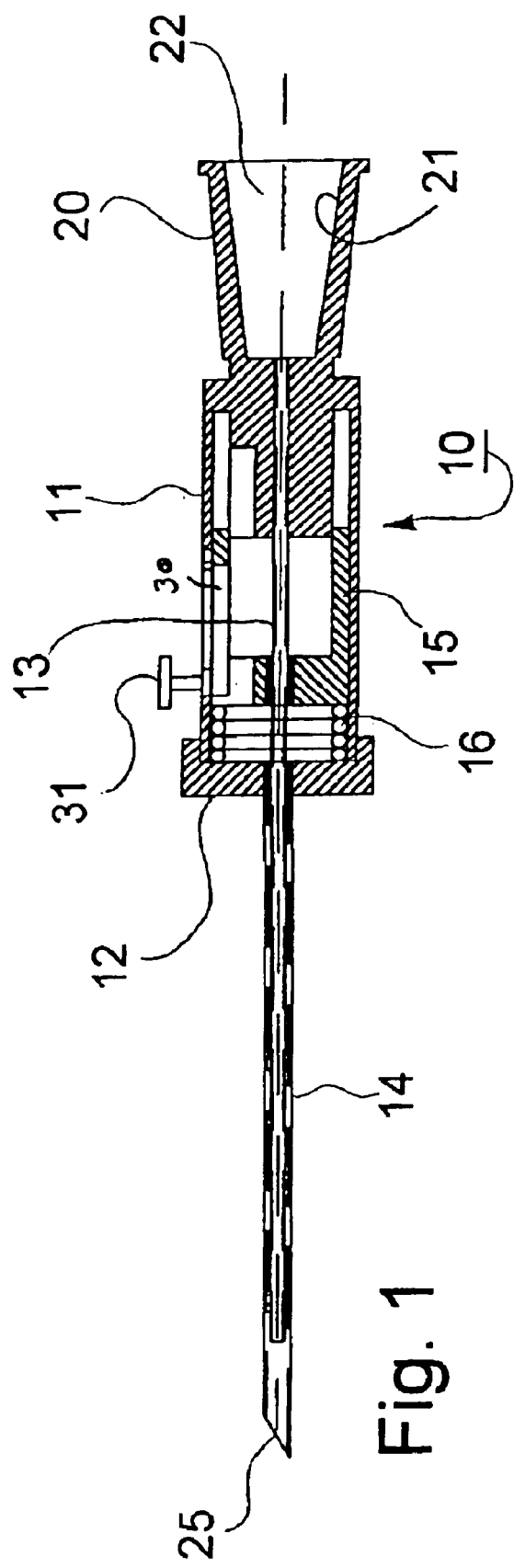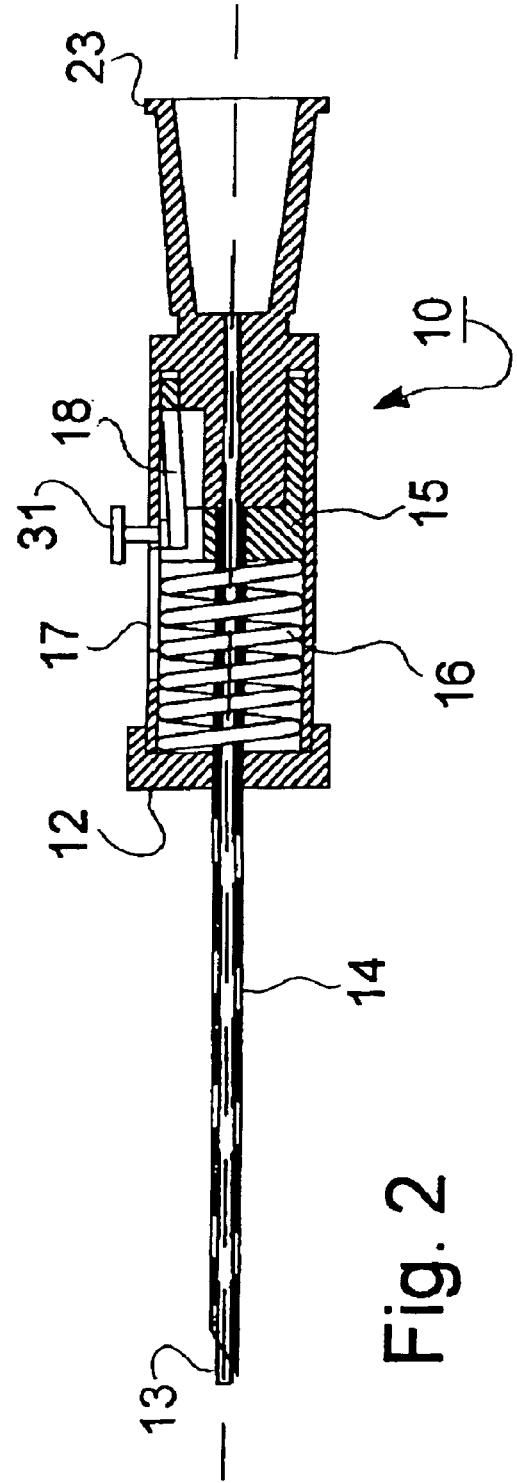

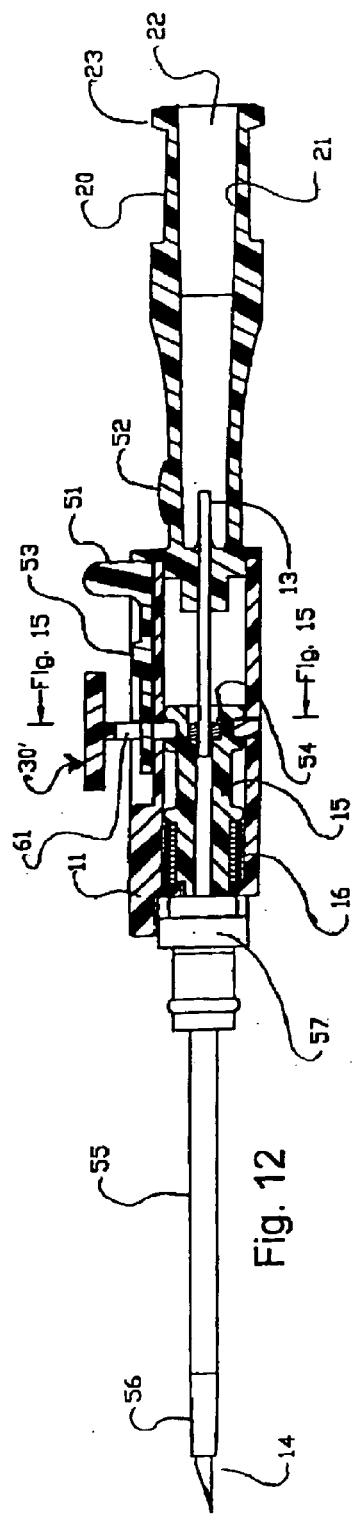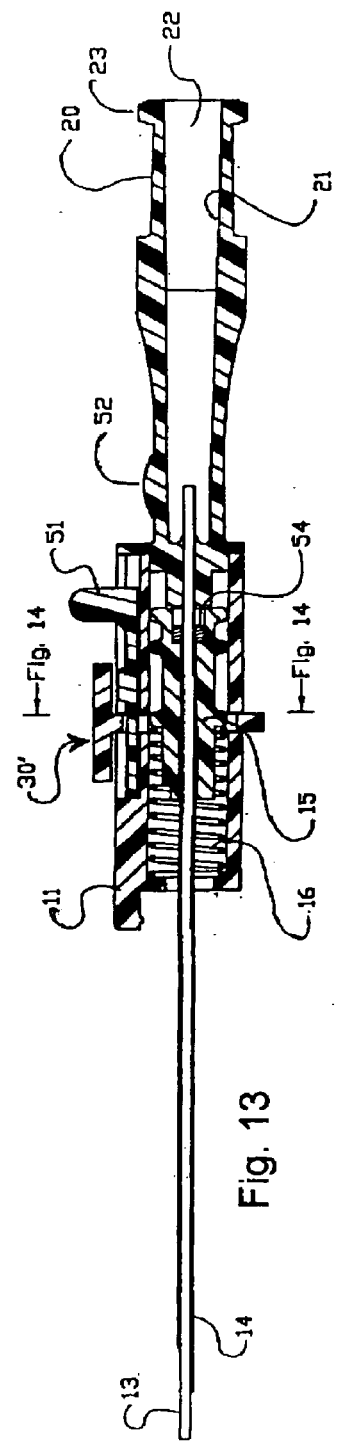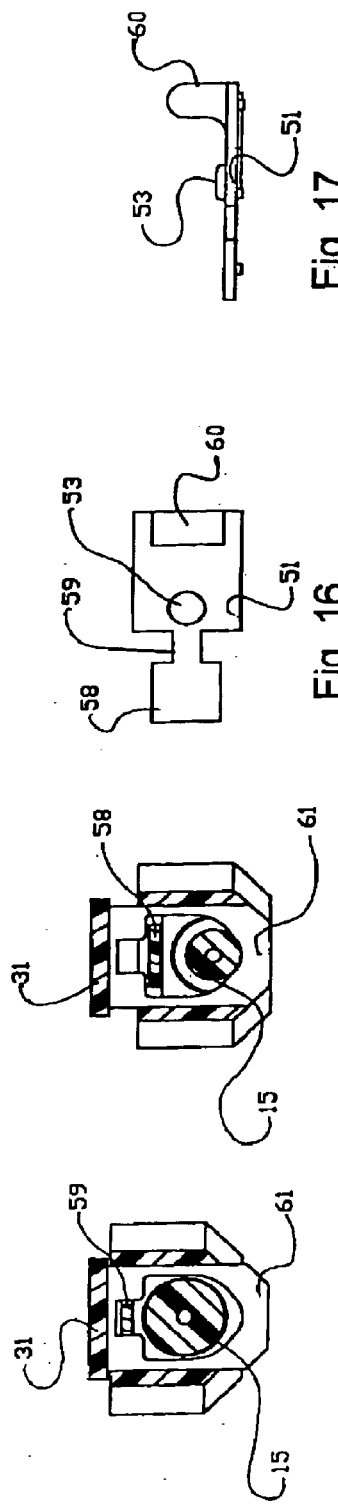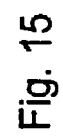

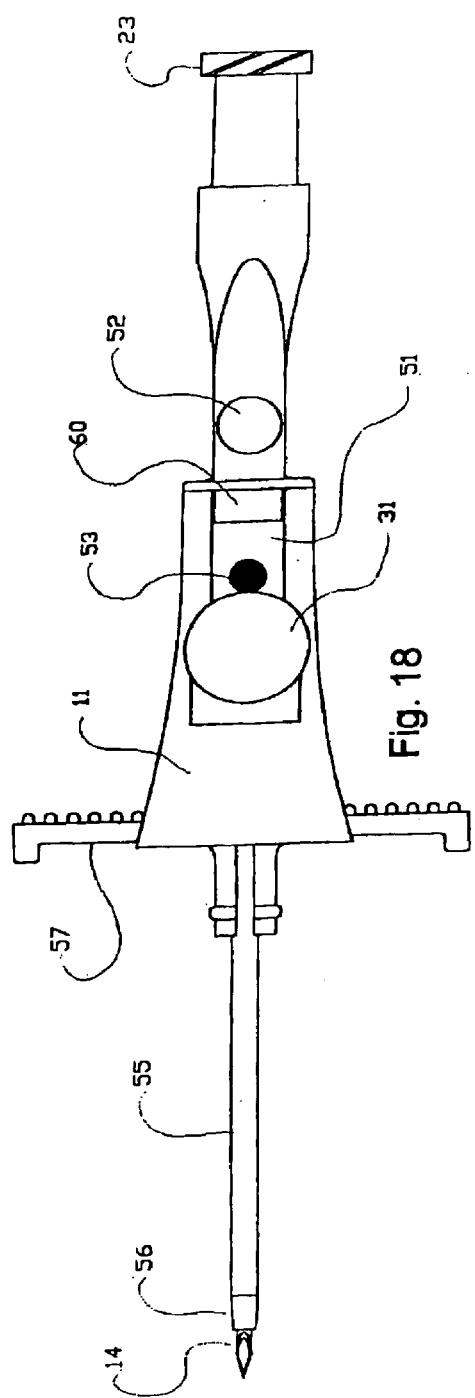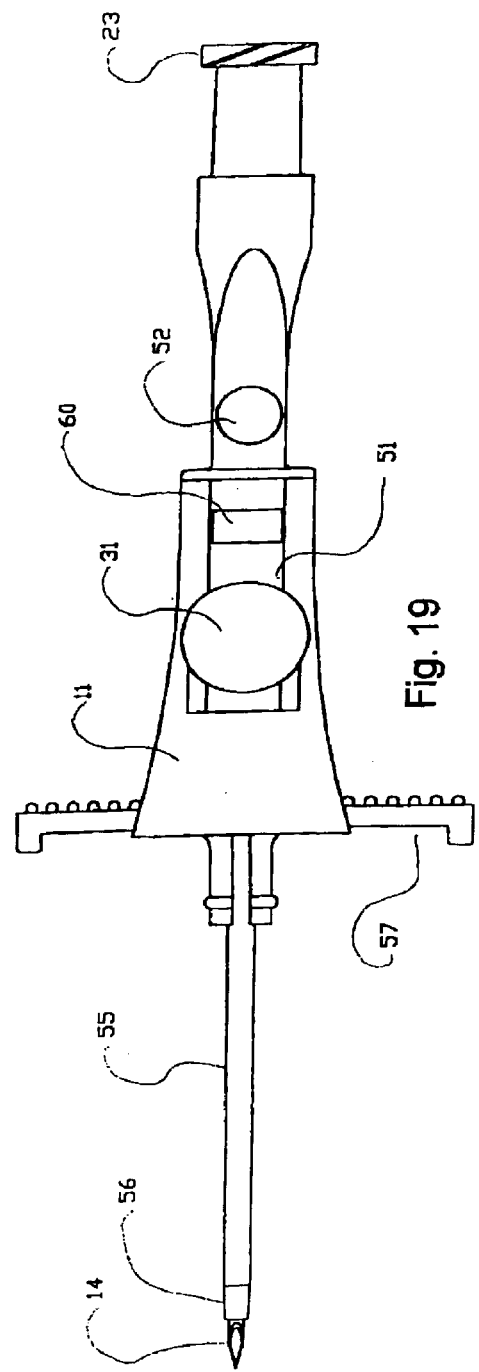

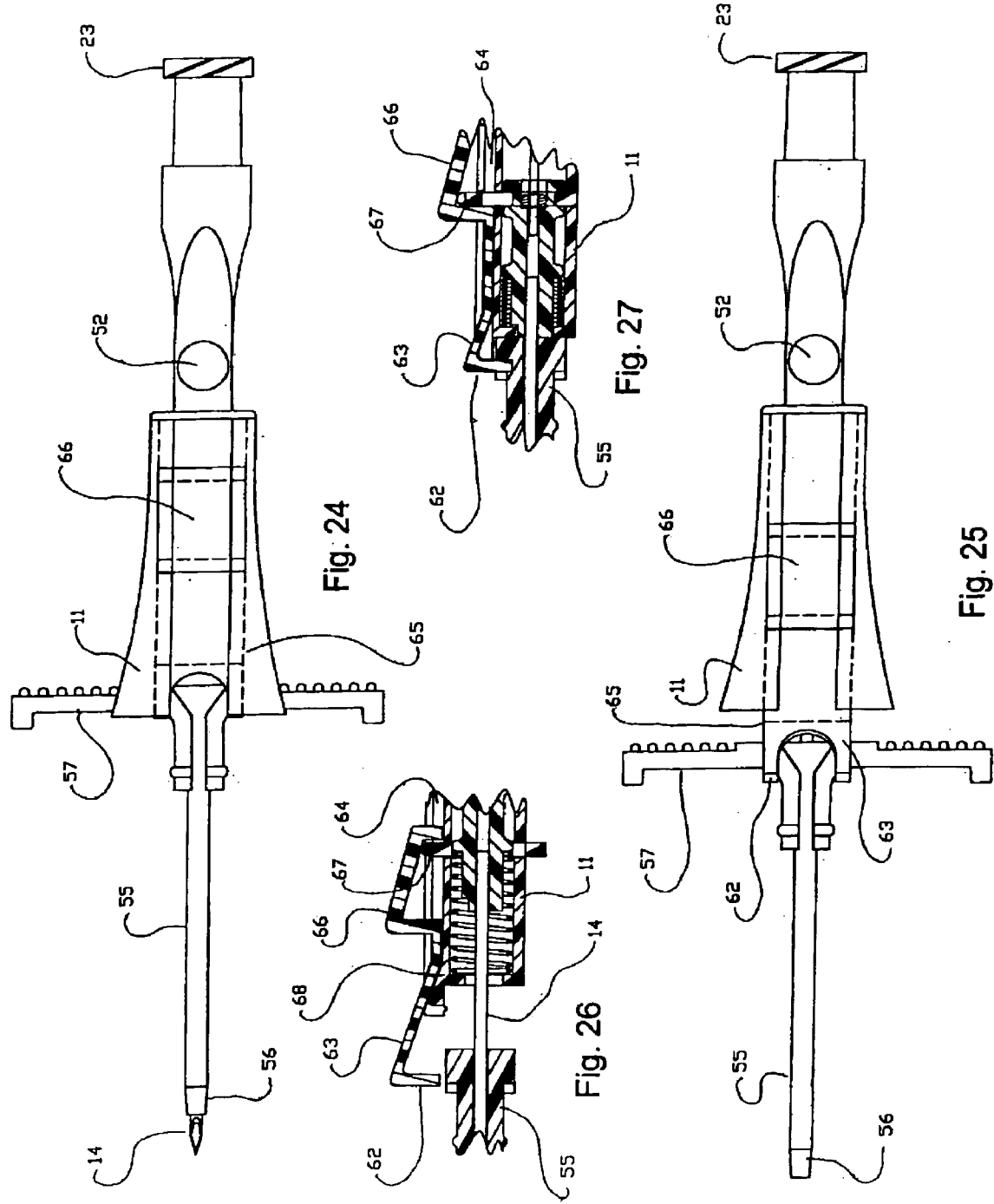

SAFETY NEEDLE

This application claims the benefit of provisional patent application No. 60/265,400, filed Jan. 31, 2001.

This invention relates to a safety needle. More particularly, this invention relates to a safety needle employing a blunt cannula to protect a sharp edged needle.

As is known, one major problem with hypodermic needles as well as other needles is the threat of cutting oneself or another thereby exposing a blood vessel to the environment. This has become especially important in a hospital atmosphere where AIDS patients or AIDS members of a staff can infect others by having their blood interact, for example, by touching another person.

Various techniques have been proposed to overcome this problem. For example, in some cases, use has been made of a shield or cap which is placed over a needle after use. Generally, this is intended to only allow a one-time use of the needle with an automatic covering system which prevents further use. However, during actual use of such a needle the needle does not remain totally protected. Further, if the needle is re-used, there is no provision to sheath the needle.

U.S. Pat. No. 4,629,453 describes a protection device for a hypodermic needle which uses a protective cap which can be fitted over a needle when the needle is not in use.

U.S. Pat. No. 4,735,618 describes a protective enclosure for hypodermic needles which employs a cap-like needle guard which is positioned about a free end of a needle while being connected via collapsible arms to a tubular sleeve mounted about a needle housing. When in use, the cap is pressed against a patient under a sufficient force to cause collapsing of the collapsible arms so that the cap slides back over the needle. However, when not intended for use, any accidental pushing in on the cap can cause an inadvertent needle stick.

U.S. Pat. No. 3,134,380 describes a shielded hypodermic needle wherein a needle is sheathed within a collapsible tube so that upon collapsing of the tube, the needle is exposed. In addition, a spring is provided within the tube so as to return the collapsed tube to an extended state.

U.S. Pat. No. 4,725,267 describes the use of a resilient collapsible sheath which can be mounted over a needle to contain the needle when not in use.

U.S. Pat. No. 4,695,274 describes a removable needle attachment consisting of a needle-holding member and a safety jacket. As described, the jacket is provided with a slot which receives a guide tab of the needle-holding member so as to prevent sliding of the safety jacket back and forth on the needle holding member in order to prevent piercing of the needle through a wall of the safety jacket. However, in such a construction, as in other similar constructions, a risk of inadvertent needle sticking occurs should the guide tab be disposed in an unlocking condition within the slot.

U.S. Pat. No. 5,472,430 describes the use of a spring loaded blunt cannula which is carried within the lumen of the needle. When the spring is actuated, the blunt cannula extends beyond the needle thereby preventing it from cutting. However, in such a design there is required a twisting of the blunted cannula to achieve movement. In turn, this creates an unnatural required motion of the user to achieve movement and locking of the blunt cannula in place.

U.S. Pat. No. 5,472,430 describes a stationary needle through which a blunt needle is telescopically moved to extend beyond the sharpened edge of a sharpened needle. In this manner, the sharpened edge is protected or sheathed to prevent accidental cutting. To achieve this condition only the blunt needle may move relative to the fixed sharpened needle. When moved, the blunt needle is rotated to achieve a lock generally in the safety position. Limitations of this design include: the blunt needle must be rotated to obtain a lock and the attachable portion (normally a luer hub) is separated from the housing which performs the operation of moving the blunt needle and therefore presents a generally unmanageable obstruction to the user when manipulating the blunt needle. It has been found that the user has difficulty in placing the sharpened needle in a safety position by rotating the detent to activate the spring or arming the sharpened needle again by a rotation of the detent prior to movement of the blunt needle. Should the moveable member be the sharpened needle, then there is the danger that rotating the sharpened needle will result in damage if the sharpened needle is within the body or to the user if a part of the user's body comes in contact with the needle edge.

Accordingly, it is an object of the invention to provide a needle assembly with a protective interior blunt needle.

It is another object of the invention to prevent inadvertent passage of a needle from a protective state outside of a blunt needle to an armed state capable of cutting.

It is another object of the invention to provide for movement of a sharpened needle without rotation to achieve a lock.

It is another object of this invention to provide a natural means for a user to move a needle from an armed state to an unarmed state.

Briefly, the invention provides a safety needle that is comprised of a housing, a blunt cannula mounted in and extending from the housing, a slider movably mounted in the housing and on the blunt cannula for movement between a locked position and an unlocked position and a needle mounted in and extending from the slider in concentric relation to the blunt cannula. The needle has a sharpened end projecting beyond the blunt cannula in the locked position of the slider and is retracted over the blunt cannula in the unlocked position of the slider.

In accordance with the invention, the safety needle has a spring in the housing for biasing the slider from the locked position towards the unlocked position. The invention also provides a manually operated actuator that is movable between a first position blocking movement of the slider from the locked position to the unlocked position and a second position allowing movement of the slider from the locked position to the unlocked position under a biasing force of the spring.

In one embodiment, the housing has an elongated slot while the actuator is mounted on the slider to move transversely within the slot of the housing between the first and second positions thereof. In particular, the slot has an enlarged aperture disposed in a location corresponding to the locked position of the slider, while the actuator has a stem that slides within the slot, as well as an enlarged boss for seating in the enlarged aperture in the first position of the actuator. Thus, when the boss is seated in the enlarged aperture, the slider is restrained against movement under the biasing force of the spring. However, when the boss is moved out of the enlarged aperture, the stem is free to slide within the slot in the housing under the biasing force of the spring. This, in turn, allows the slider to move within the housing.

In this embodiment, the actuator is integral with the slider. To this end, the actuator has an arm that receives the stem at one end and that extends from the slider at the opposite end in cantilever relation. In addition, the actuator includes a button on the stem for manual pushing of the stem into the housing in order to move the boss out of the enlarged aperture.

In operation, when the safety needle is used in making a venipuncture in a patient, the needle is in an extended position relative to the blunt cannula so as to project beyond the cannula. Upon depressing the button of the actuator, the slider moves under the bias of the spring to retract the needle over the cannula so that the cannula protects against an inadvertent "stick".

In another embodiment, the actuator is slidably mounted transversely within the housing to move between a position in which the slider is locked and a position in which the slider is unlocked. In this embodiment, the slider has a groove while the actuator has a stem selectively positioned in the groove in the first position of the actuator and positioned outside the groove in the second position of the actuator.

For example, in this embodiment, the groove in the slider is an annular groove and the stem has an aperture for passage of the slider therethrough. Thus, when the actuator is in a raised first position, the stem fits into the groove of the slider to prevent the slider from moving under the bias of the spring. When the actuator is depressed, the stem moves out of the groove of the slider to permit the slider to pass through the aperture in the stem under the biasing force of the spring.

In this embodiment, a guard is slidably mounted on the housing for movement between a blocking position to block movement of the actuator and a release position to allow movement of the actuator. This reduces the risk that the actuator may be inadvertently actuated.

In order to have the actuator cooperate with the guard, the stem has a reduced recess communicating with the aperture through which the slider passes. In addition, the guard has a body extending into the aperture in the blocking position to block movement of the actuator and a reduced section extending into the recess of the actuator when in the released position to unlock the actuator.

Thus, when the guard is in the blocking position, the body on the guard is disposed when the aperture in the stem of the actuator to prevent the actuator from being depressed into the housing. When the guard is moved into the unblocking position, the reduced section of the guard is aligned with the reduced recess in the actuator stem, the actuator is then free to be pushed into the housing so that the reduced section of the guard is accommodated within the reduced recess while the stem of the actuator moves into a position to allow the slider to move through the aperture in the actuator stem under the biasing force of the spring.

In this embodiment, the actuator includes a button on the stem for manual pushing of the stem into the housing. In addition, the guard is provided with an indicator which is positioned outside the button when the guard is in the blocking position and is positioned under the button when the guard is in the release position.

In still another embodiment, wherein the actuator is separate from the slider, an actuator depressor is slidably mounted on the housing for moving the actuator into the housing. In this embodiment, the actuator depressor includes a recess receiving the actuator and a sloped wall in the recess abutting the actuator whereby, upon movement of the depressor along the housing, the sloped wall moves the actuator into the housing and into the second position thereof.

In this latter embodiment, the actuator depressor serves to prevent inadvertent depressing of the actuator into the housing by bridging over the actuator. Also, the actuator depressor provides a surface which may be manually actuated to slide along the housing in order to move the actuator into the housing to release the spring biased slider.

A sheath may be slidably mounted on and over the needle outside the housing. Typically, the safety needle would be withdrawn from the sheath to leave the sheath in place. In order to provide for an automatic actuation of a spring-biased slider, a gripper arm extends from the actuator depressor to selectively engage the sheath. Thus, as the housing is pulled away from the sheath, the gripper arm is initially in engagement with the sheath so that the actuator depressor is pulled along the housing, thereby depressing the actuator into the housing to unlock the spring-biased slider. Thus, once the housing has been separated from the sheath, the needle is automatically retracted over the blunt cannula into the protected position.

In order to facilitate disengagement of the gripper arm on the actuator depressor from the sheath, the gripper arm may be spring-mounted on the actuator depressor to be biased away from the sheath in a predetermined location of the actuator depressor on the housing.

These and other advantages will become more apparent from the following description taken in conjunction with the drawings wherein:

FIG. 1 illustrates a cross sectional view of a product constructed in accordance with the invention for use as a hypodermic needle with a sharpened edge exposed beyond a blunt cannula;.

FIG. 2 illustrates a cross sectional view of the product of FIG. 1 with the blunt cannula exposed;

FIG. 12 illustrates a partial cross-sectional view of a further embodiment of a safety needle constructed in accordance with the invention;

FIG. 13 illustrates a view of the safety needle of FIG. 12 with a needle retracted over a blunt cannula;

FIG. 14 illustrates a view taken on line 14—14 of FIG. 13;

FIG. 15 illustrates a view taken on line 15—15 of FIG. 12;

FIG. 16 illustrates a top view of an actuator guard constructed in accordance with the invention;

FIG. 17 illustrates a side view of the actuator guard of FIG. 16;

FIG. 18 illustrates a top view of the safety needle of FIG. 12 in a position of use;

FIG. 19 illustrates a top view of the safety needle of FIGS. 12 and 13 with the actuator guard in an unlocked position;

FIG. 24 illustrates a top view of the safety needle of FIG. 20;

FIG. 25 illustrates a top view of the safety needle in the position shown in FIG. 21;

FIG. 26 illustrates a modified gripper arm between an actuator depressor and a sheath in accordance with the invention; and FIG. 27 illustrates a cross-sectional view of the embodiment of FIG. 26 in a locked position.

Figure 7:
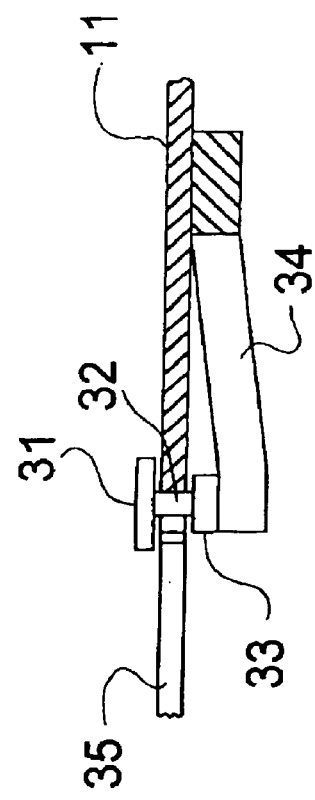
FIG. 7 is a top view of a portion of the actuator assembly secured in the permanent locking portion of the slot.

Referring to FIGS. 1 and 2, safety needle 10 includes a one-piece plastic housing 11 in which a blunt cannula is mounted and which extends from the housing 11. The blunt cannula 13 is insert-molded within the housing 11 or may be adhesively sealed in place, such as, with epoxy or similar adhesive.

The safety needle 10 also has a plastic, cylindrical slider 15 moveably mounted in the housing 11 about the cannula 13. In addition, a hollow, stainless steel needle is mounted in and extends from the slider 15 in concentric relation to the blunt cannula 13. The needle 14 is preferably insert-molded upon the axis of the slider 15 or may be adhesively secured to the slider 15. Depending upon the thickness of the annular space between the inner diameter of the needle 14 and the outer diameter of the cannula 13, a seal may or may not be required at the exit end of the needle 14. As illustrated, the exit end of the needle 14 terminates at the face of the slider 15. Should a seal be required (not shown), a plastic ring may be attached to the slider 15 with a slight interference fit about the needle 14 to prevent leakage. Such a plastic ring may be made of a soft plastic, such as polyethylene. Other means may also include the use of an O-ring or an elastomeric wiper ring.

As illustrated in FIGS. 1 and 2, the slider 15 is slideably mounted within the housing to move between a locked position (FIG. 1) and an unlocked position (FIG. 2) under the biasing force of a spring 16. As indicated, the spring 16 is a helical spring that is placed in the housing 11 distal to and against the slider 15. For purposes of assembly, the housing 11 has an opened end to allow the slider 15 and spring 16 to be fitted therein. Accordingly, an apertured end cap 12 is placed over the needle 14 and is secured over the distal end of the housing 11, thereby compressing the spring 16. The end cap is locked in place using a suitable sealing means. For example, the end cap 12 may be secured to the housing 11 by ultrasonic sealing of the two parts together.

Figure 8:
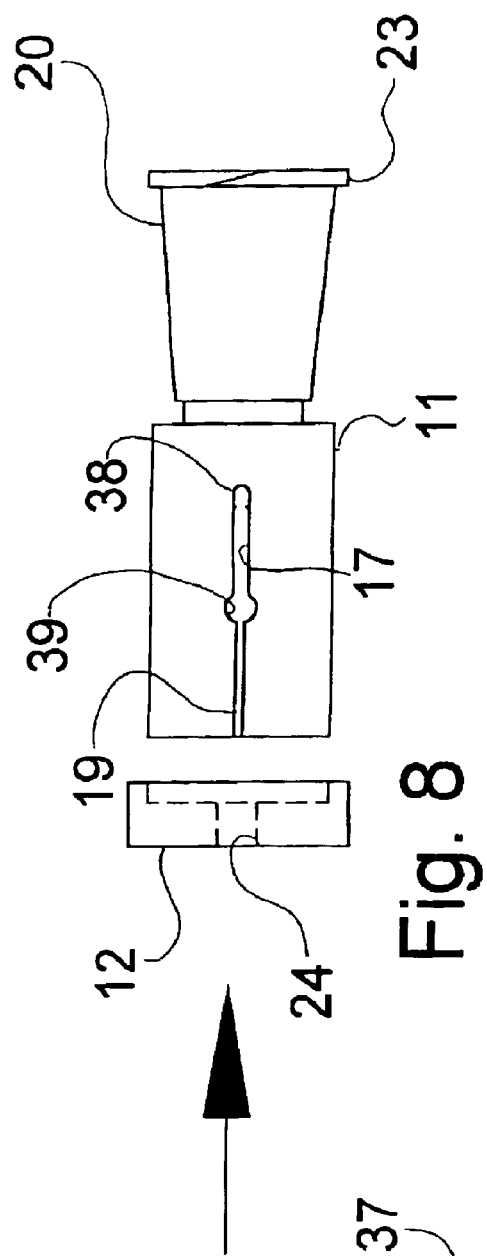
FIG. 8 is an exploded top view of the safety needle and cap of FIG. 1.
Figure 9:
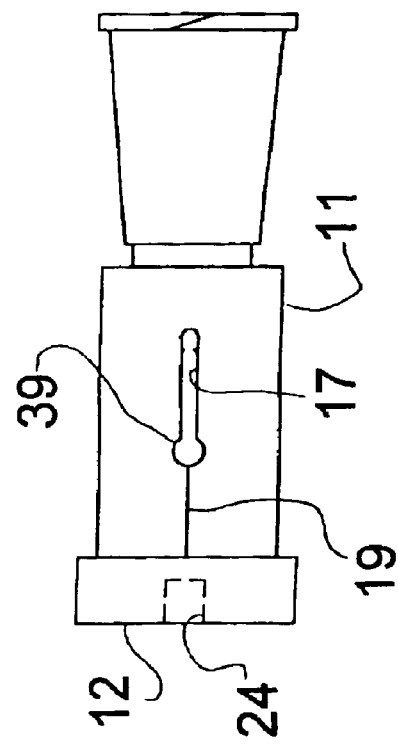
FIG. 9 illustrates the housing of FIG. 8 with the end cap in place.

Referring to FIGS. 8 and 9, the housing 11 is provided with an elongated slot having a narrow entry portion 19. When the end cap 12 is mounted in place, the slot 19 tends to close (FIG. 9). The elongated slot also has an enlarged aperture 39 (see FIG. 8) disposed in a location corresponding to the locked position of the slider 15, a widened portion 17 and a locking aperture 38 for purposes as described below.

Referring to FIG. 1, a manually operated actuator 30 is movable between a first position, as indicated in FIG. 1, blocking movement of the slider 15 from a locked position to the unlocked position, and a second position, as indicated in FIG. 2, allowing movement of the slider 15 from the locked position to the unlocked position under the biasing force of the spring 16.

Referring to FIGS. 1 and 2, the actuator 30 is integrally formed with the slider 15. In this respect, the actuator 30 has an arm 34 that extends from the slider 15 in cantilever manner within a slot of the slider 15. The free end of the arm 34 carries a stem 32 for sliding within the slot of the housing 11, as well as an enlarged boss 33 for seating in the enlarged aperture 39 within the slot. The stem 32 also carries an enlarged button 31.

Figure 5:
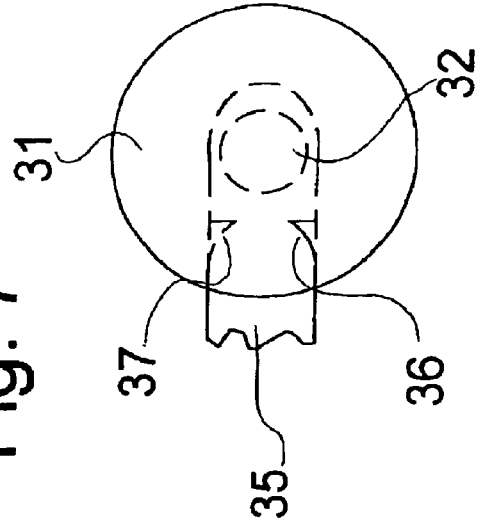
FIG. 5 illustrates the actuator assembly in a stem locked position exposing the blunt cannul.
Figure 4:
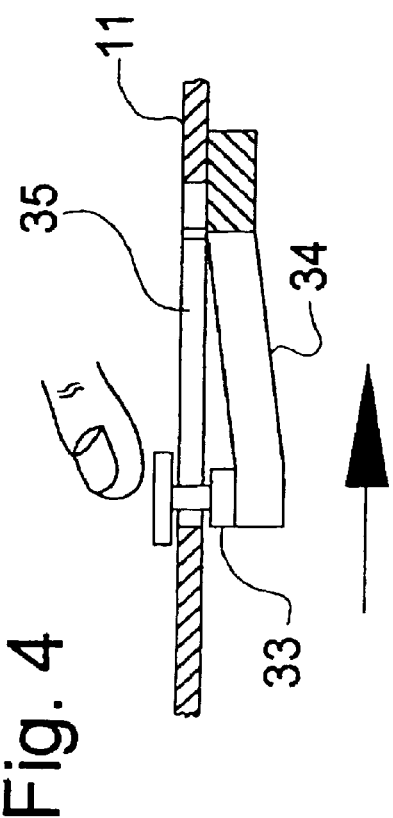
FIG. 4 illustrates the actuator assembly in an activated position.

Referring to FIG. 4, when the button 31 of the actuator 30 is depressed, the boss 33 is moved out of the plane of the enlarged aperture 39 in the slot The stem 31 then moves into the plane of the widened portion 19 of the slot and is able to slide along with the remainder of the slider 15 under the biasing force of the spring 16 into the position as illustrated in FIG. 5.

Figure 3:
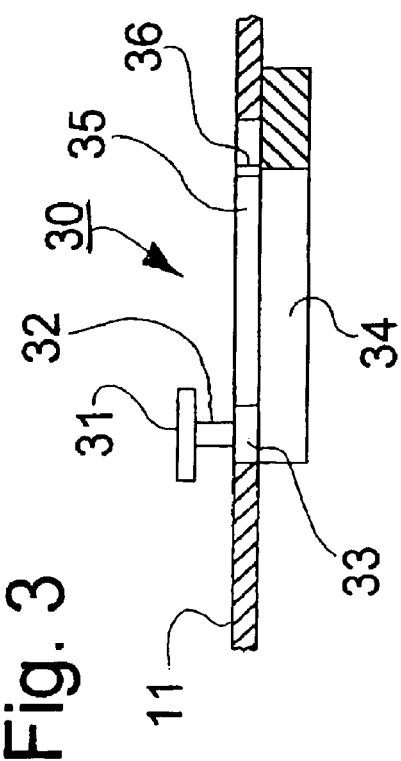
FIG. 3 illustrates in partial cross section a locking actuator assembly for exposing the sharpened edge of the needle.
Figure 6:
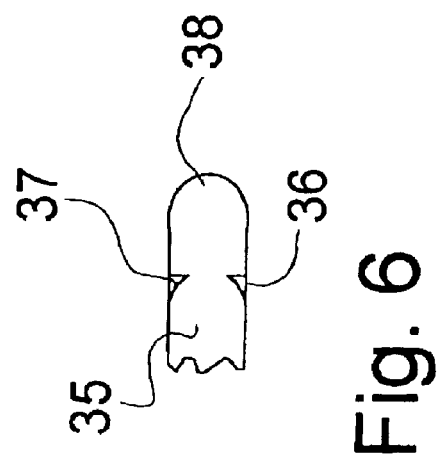
FIG. 6 illustrates in a fragmentary view a pair of detents for separating one portion of a slot in the actuator assembly from a permanent locking portion of the slot.

The as-fabricated condition of the actuator 30 provides for the boss 33 to be within the enlarged aperture 39. Manual pressure on the button 31 in a direction as indicated in FIG. 4, causes the arm 34 to flex downwardly into the housing 11 so that the boss 33 leaves the aperture 39 and is replaced by the stem 32. Since the widened portion 17 of the slot is larger than the diameter of the stem 32, the slider 15 moves to the right, as shown by the arrow in FIG. 4 under the bias of the spring 16. During this movement, the stem 32 moves through the slot and has sufficient momentum to slightly open a pair of detents 36, 37 in the side walls of the slot and come to a stop in the locking stem aperture 38 (see FIGS. 6, 7 and 8). The detents 36, 37, as indicated in FIG. 6, are unidirectional and permanently prevent the stem 32 from exiting the stem locking aperture 38. Should one desire to re-arm the safety needle, the detents 36, 37 would not be included, and the user would simply push the button 31 forward until the boss aperture 39 is reached, at which location, the boss 33 would reenter, as indicated in FIG. 3 under the biasing force of the arm 34.

As indicated in FIG. 8, the narrowed entry portion 19 of the slot expands to allow the stem 33 of the actuator 30 to move into the position shown in FIG. 1.

Referring to FIG. 1, the proximal end of the housing 11 includes a female luer connector 20, which may have a luer lock 23 and bore 22. The blunt hollow cannula 13 terminates at and is in fluid communication with the distal end of the female luer connector bore 22.

The actuator 30 allows the needle 14 to be exposed and useable for puncture. Upon actuation of the actuator 30, the needle 14 is retracted over the blunt cannula 13 so as to be disposed in a protected manner.

Figure 10:
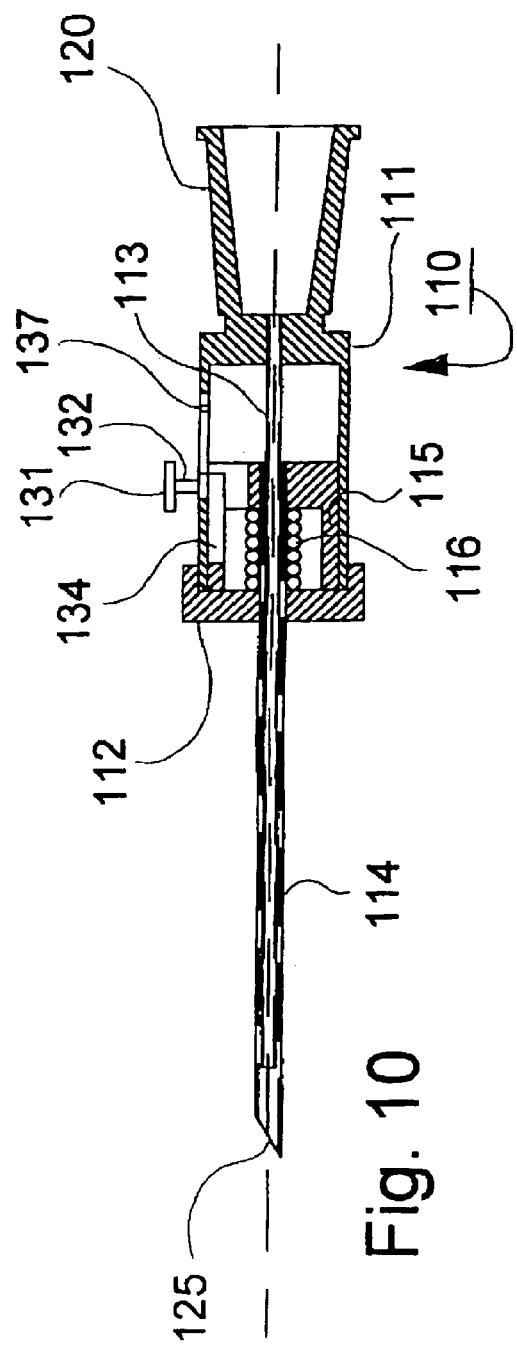
FIG. 10 illustrates another embodiment of the safety needle in accordance with the invention in which the slider assembly is reversed with the cutting edge of the needle exposed.
Figure 11:
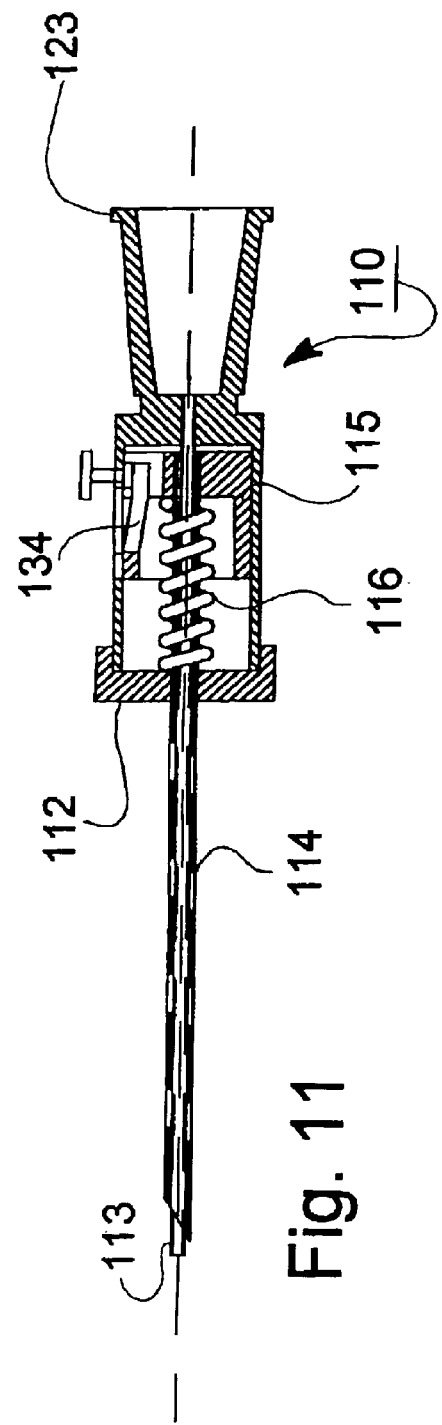
FIG. 11 illustrates the safety needle of FIG. 10 with the blunt cannula exposed and spring expanded.

Referring to FIGS. 10 and 11, wherein like reference characters indicate like parts as above, the slider 15 may be mounted in a reversed manner from that as illustrated in FIG. 1. In this embodiment, the spring 16 is positioned within a cup portion of the slider 15.

Referring to FIG. 12, wherein like reference characters indicate like parts as above, the safety needle employs an actuator 30' that is not integral with the slider 15 but separately mounted in the housing 11. As illustrated, the actuator 30' is slideably mounted transversely within the housing 11 to move between a first position, as shown in FIG. 12, blocking movement of the slider 15 to an unlocked position, as illustrated in FIG. 13, allowing movement of the slider 15 under the biasing force of the spring 16. To this end, the actuator 30' has a stem 61 that is provided with an aperture for passage of the slider 15 therethrough, as illustrated in FIG. 14. The slider 15 has an annular groove to selectively receive the stem 61, as indicated in FIG. 15.

When the actuator 30' is in the raised position illustrated in FIGS. 12 and 15, the stem 61 is positioned within the groove of the slider 15 so that the slider 15 is not able to move under the force of the spring 16. When the actuator 30' is depressed into the housing 11, as indicated in FIGS. 13 and 14, the stem 61 moves out of the groove of the slider 15 so that the slider 15 is free to move through the aperture in the stem 61 under the biasing force of the spring 16.

Referring to FIG. 12, a guard 51 is slideably mounted on the housing 11 for movement between a blocking position, blocking movement of the actuator 30', as illustrated in FIGS. 12 and 15, and a release position to allow movement of the actuator 30', as indicated in FIGS. 13 and 14.

Referring to FIG. 16, the actuator guard 51 is of generally flat shape with a body 58 sized to extend into the aperture in the stem 61 (see FIG. 15) to thereby block a downward movement of the stem 61. The guard 51 also has a reduced intermediate section 59 that is sized to move into a reduced recess in the stem 61 that communicates with the aperture in the stem (see FIGS. 14 and 15). Thus, when the guard 51 is slid to the left, as viewed in FIG. 12, the reduced section 59 moves into alignment with the reduced recess in the stem 61 of the actuator 30'. When the button 31 of the actuator is depressed, the stem 61 moves downwardly into the position shown in FIG. 14, with the reduced section 59 of the guard being accommodated in the reduced recess of the stem 61.

Referring to FIGS. 16 and 17, the guard 51 also has an indicator 53 thereon. For example, the indicator 53 may be a green color. When the guard 51 is in the blocking position, the indicator 53 is exposed to view, as indicated in FIG. 18. When the guard 51 has been moved to the unblocking position, the indicator 53 moves under the button 31 out of view, as indicated in FIG. 19.

Referring to FIG. 12, the female luer connector 23 also has a magnifier 52 that assists the user in detecting blood at the exit of the blunt cannula 13, that is, in a flashback chamber within the connector 23.

Referring to FIG. 12, a sheath is disposed over the needle 14. As indicated, the sheath includes a plastic tube 55 having a beveled distal end 56 and a pair of peel-away plastic wings 57 (see FIGS. 18 and 19). The sheath is secured to the needle 14 by a compression fit of the beveled distal end 56 to the needle 14.

The housing 11 also has an overhang that acts to stabilize the wings 57.

As shown in FIG. 12, a seal ring 54 is disposed within the slider 15 about the cannula 13. This seal ring 54 moves axially along the blunt cannula 13 to provide a seal between the cannula 13 and the needle 14.

After venipuncture, the sheath 55 is removed by sliding the sheath 55 off the needle 14.

Referring to FIGS. 1 and 2, in operation, the sharpened needle 14 moves about 0.375" from the boss hole 39 to the stem locking hole 38 position. The normal annular thickness between the outer diameter of the blunt cannula 13 and the inner diameter of the stainless steel sharpened needle 14 is approximately 0.001".

The spring constant for the spring 16 is chosen to overcome the physical interference/of the stem 32 to the detents 36,37 as the stem 32 travels from the boss hole 39 to the stem locking hole 38.

The boss 33 may have a diameter of 0.155" and a thickness of 0.030–0.040". The boss hole 39 may have a diameter of 0.160" and a thickness of 0.030–0.045". The cut out distance from the base of the arm 34 to the central section of the slider 15 which supports the needle 14 may be 0.035–0.45". The outer diameter of the housing 11 may be 0.300". The length of the housing 11 may be 1.2". The housing may be composed of an engineering plastic such as polycarbonate, modified acrylic, polyester copolymer or the like.

The button 31 may be formed to provide for finger curvature or be raised for maximum pressure concentration.

The slot 17,19 being in a straight line prevents any circumferential movement of the needle 14 during actuation from the armed to an unarmed position.

In use, the safety needle is supplied pre-armed as shown in FIG. 1 with a protective sheath over the sharpened needle 14. Normally, the product is removed from a sterile protective package and attached at the female luer connector 20 to the male luer adaptor of a syringe. Generally, the syringe has been pre-filled with the medication of choice. The protective sheath is now removed and the patient's skin and blood vessel is punctured in the normal manner. After dispensing the medicament, the user generally places an absorbent gauze over the puncture site, holds the gauze and patients extremity with one hand and grasps the needle hub and neck of the syringe with the other hand. At that time, the button 31 is depressed allowing the sharpened needle to be moved by the spring 16 into a safe (non-cutting condition) position with the blunt cannula 13 exposed. The safety needle assdi nbly is then removed from the patient and can safely be disposed of without concern for inadvertent cutting of the patient or user. The needle 14 may be disconnected from the syringe prior to disposal if desired.

Figure 20:
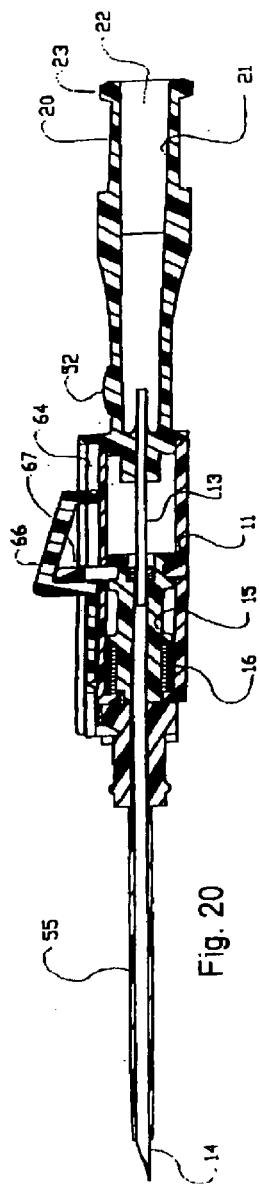
FIG. 20 illustrates a cross-sectional view of a further embodiment of a safety needle constructed in accordance with the invention.

Referring to FIG. 20, wherein like reference characters indicate like parts as above, the actuator 67 is flat and is otherwise constructed in the manner of the actuator 30' of FIG. 12. That is to say, the actuator 67 has an aperture that allows the slider 15 to slide therethrough and that is otherwise disposed within an annular groove of the slider 15 for blocking purposes, as described above.

Figure 21:
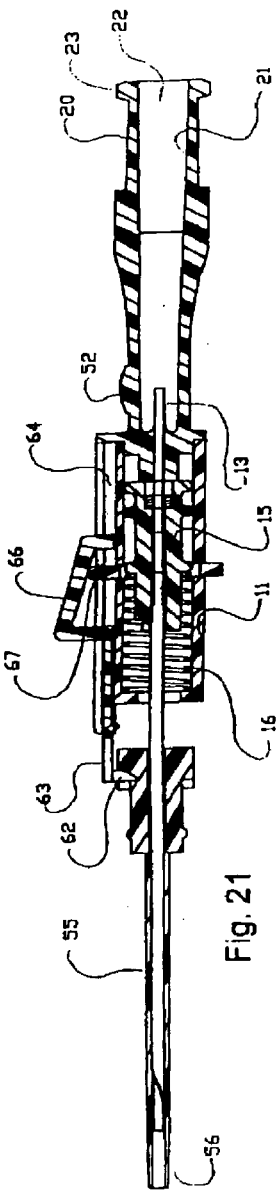
FIG. 21 illustrates a view of the safety needle of FIG. 20 with the actuator in an actuated position in accordance with the invention.

As illustrated, an actuator depressor 66 is slideably mounted in a track 64 in the housing 11 for moving the actuator 67 into the housing 11. As illustrated, the actuator depressor 66 includes an internal recess that receives the actuator 67 in a bridging-over manner. In addition, the depressor 66 has a sloped wall in the recess that abuts the actuator 67. Thus, upon movement of the depressor 66 along the housing 11 from the position shown in FIG. 20 to the position shown in FIG. 21, the sloped wall moves the actuator 67 into the housing 11 and into an unlocked position relative to the slider 15. The slider 15 is thus able to move through the aperture in the actuator 67 under the biasing force of the spring 16 (see FIG. 21).

When the safety needle is in the condition illustrated in FIG. 20, a venipuncture may be performed. After venipuncture, the sheath 55 is removed by sliding the sheath 55 off the needle 14 In this embodiment, a gripper arm 63 extends from the actuator depressor 66 into engagement with the sheath 55 via a wing 62. Thus, upon movement of the sheath 55 off the needle 14, the sheath 55 pulls the actuator depressor 66 via the gripper arm 63. This, in turn, causes the actuator depressor 66 to push the actuator 67 into the housing 11 to release the slider 15.

Figure 22:
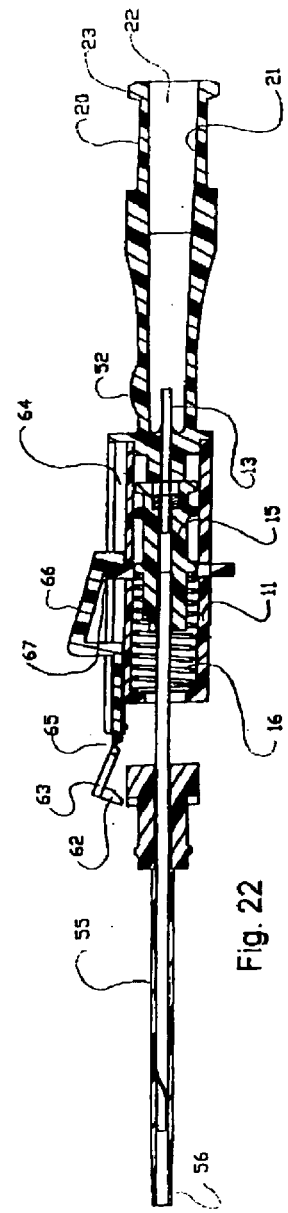
FIG. 22 illustrates a view similar to FIG. 21 with a gripper element being released from a sheath employed about a needle in accordance with the invention.

Referring to FIG. 22, in order to effect release of the gripper arm 63 from the sheath 55, the gripper arm 63 is spring-mounted about a hinge 65 on the actuator depressor 66 so as to move away from engagement with the sheath 55.

Figure 23:
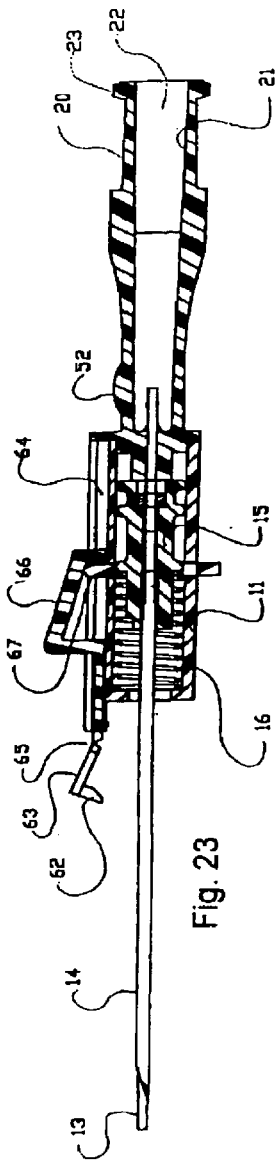
FIG. 23 illustrates a view similar to FIG. 22 with the sheath removed from the safety needle.

As indicated in FIG. 23, once the sheath has been separated from the needle 14, the slider 15 has been spring-biased into a position that retracts the needle 14 over the blunt cannula 13. The safety needle is thus in a safe condition.

Referring to FIG. 24, typically, when the sheath 55 is in place, the actuator depressor 66 is in a blocking condition. FIG. 25 illustrates the actuator depressor 66 in the position corresponding to FIG. 22.

Referring to FIGS. 26 and 27, wherein like reference characters indicate like parts as above, the gripper arm 63 may be integral with the actuator depressor 66. In this embodiment, a ramp 68 is provided on the overhang of the housing 11 along which the gripper arm 63 slides as the actuator depressor 66 moves from a forward position as shown in FIG. 26 to a rear position as shown in FIG. 27. In this respect, the gripper arm 63 is resilient so as to flex upwardly from the position shown in FIG. 27 to the position shown in FIG. 26 when sliding along the ramp 68. During movement of the gripper arm 63 up the ramp 68, that is into the position shown in FIG. 26, the gripper wing 62 rises upwardly as shown to move out of the plane of the sheet 55. The sheet 55 may then be removed from the needle 14.

The invention thus provides a safety needle in which a manually operated actuator can be moved from a first position to a second position in order to allow a spring-biased slider to be fired so as to pull a needle over a blunt cannula for safety purposes.

Other applications for this safety needle product include: introducer needle for use particularly in Seldinger procedures, administration of fluids and medicaments into elastomeric injection ports, spinal and anesthesia needle procedures. This product may also be used in conjunction with IV catheter placement products especially the over the needle type and in conjunction with dilators and dilator sheaths for placement of P1CC lines.

What is claimed is:

1. A safety needle comprising a housing;

a blunt cannula mounted in and extending from said housing;

a slider movably mounted in said housing and on said blunt cannula for movement between a locked position and an unlocked position;

a needle mounted in and extending from said slider in concentric relation to said blunt cannula, said needle having a sharpened end projecting beyond said blunt cannula in said locked position of said slider and retracted over said blunt cannula in said unlocked position of said slider;

a spring in said housing for biasing said slider from said locked position towards said unlocked position;

a manually operated actuator movable between a first position blocking movement of said slider from said locked position to said unlocked position and a second position allowing movement of said slider from said locked position to said unlocked position under a biasing force of said spring.

2. A safety needle as set forth in claim 1 wherein said actuator is slidably mounted transversely within said housing between said positions thereof.

3. A safety needle as set forth in claim 2 which further comprises a guard slidably mounted on said housing for movement between a blocking position blocking movement of said actuator and a release position to allow movement of said actuator.

4. A safety needle as set forth in claim 3 wherein said actuator has a stem with an aperture and a reduced recess communicating with said aperture and said guard has a body extending into said aperture in said blocking position to block movement of said actuator and a reduced section extending into said recess in said release position to unlock said actuator.

5. A safety needle as set forth in claim 4 wherein said actuator includes a button on said stem for manual pushing of said stem into said housing.

6. A safety needle as set forth in claim 5 wherein said guard has an indicator thereon, said indicator being positioned outside said button in said blocking position and under said button in said release position.

7. A safety needle as set forth in claim 4 wherein said slider passes through said aperture in said actuator stem and has an annular groove for receiving said stem in said first position of said actuator.

8. A safety needle as set forth in claim 2 wherein said slider has a groove therein and said actuator has a stem selectively positioned in said groove in said first position and positioned outside said groove in said second position.

9. A safety needle as set forth in claim 8 wherein said groove in said slider is an annular groove and said stem has an aperture for passage of said slider therethrough.

10. A safety needle as set forth in claim 2 which further comprises an actuator depressor slidably mounted on said housing for moving said actuator into said housing.

11. A safety needle as set forth in claim 10 wherein said actuator depressor includes a recess receiving said actuator and a sloped wall in said recess abutting said actuator whereby upon movement of said depressor along said housing, said sloped wall moves said actuator into said housing and into said second position thereof.

12. A safety needle as set forth in claim 11 which further comprises a sheath slidably mounted on and over said needle outside said housing and a gripper arm extending from said actuator depressor in selective engagement with said sheath whereby movement of said sheath off said needle pulls said actuator depressor along said housing to effect movement of said actuator into said second position thereof.

13. A safety needle as set forth in claim 1 wherein said housing has an elongated slot and wherein said actuator is mounted on said slider to move transversely within said slot of said housing between said first and second positions thereof.

14. A safety needle as set forth in claim 13 wherein said slot has an enlarged aperture disposed in a location corresponding to said locked position of said slider and said actuator has a stem for sliding within said slot and an enlarged boss for seating in said enlarged aperture in said first position of said actuator.

15. A safety needle as set forth in claim 14 wherein said actuator has an arm receiving said stem at one end thereof and extending from said slider at an opposite end thereof in cantilever relation.

16. A safety needle as set forth in claim 1 wherein said housing has an elongated slot with an enlarged aperture and said actuator includes an arm integrally extending from said slider under said slot, a stem extending from said arm through said slot, and an enlarged boss on said stem for selective positioning in said enlarged aperture to block movement of said slider relative to said housing.

17. A safety needle as set forth in claim 16 wherein said actuator includes a button on said stem for manual pushing of said stem into said housing to move said boss out of said aperture.

* * * * *